United States Patent [19]

Youngdale

[11] 4,196,213
[45] Apr. 1, 1980

[54] METHOD OF PRODUCING INFERTILITY IN MALE RODENTS

[75] Inventor: Gilbert A. Youngdale, Portage, Mich.

[73] Assignee: The Upjohn Company, Kalamazoo, Mich.

[21] Appl. No.: 920,877

[22] Filed: Jun. 28, 1978

Related U.S. Application Data

[60] Continuation of Ser. No. 736,943, Oct. 29, 1976, abandoned, which is a division of Ser. No. 601,487, Aug. 4, 1975, Pat. No. 4,012,520, which is a division of Ser. No. 386,536, Aug. 8, 1973, Pat. No. 3,930,012, which is a continuation of Ser. No. 93,383, Nov. 27, 1970, abandoned.

[51] Int. Cl.² .......................... A01N 9/12; A01N 9/24
[52] U.S. Cl. .................................. 424/275; 424/262; 424/263; 424/274; 424/276; 424/278
[58] Field of Search ............... 424/262, 263, 274, 275, 424/278, 276, 272

[56] References Cited

U.S. PATENT DOCUMENTS 2,065,125   12/1936   Dreyfus ..................... 260/340.9 X

OTHER PUBLICATIONS

J.A.C.S., 4/1952, pp. 1733 to 1736.
Chem. Abs. 1954, vol. 48, p. 13952.

Primary Examiner—Dale R. Ore
Attorney, Agent, or Firm—William G. Jameson

[57] ABSTRACT

Pharmaceutical preparations in dosage forms and animal feeds (baits) consisting essentially of pharmaceutically acceptable carriers, oral and injectable, compounded with a sublethal, yet effective, amount of a compound having the formula:

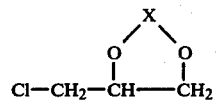

Formula I wherein X is

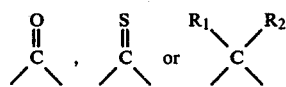

and $R_1$ and $R_2$ are the same or different and are hydrogen, alkyl of from 1 to 17 carbon atoms, alkenyl of from 2 to 17 carbon atoms, phenyl, a heterocyclic ring such as furyl, pyrrolyl, thienyl, indolyl or pyridyl, and $R_1$ and $R_2$, taken together, can be a carbocyclic ring of up to 8 carbon atoms, for inducing sterility in male mammals. Methods for preventing impregnation of females by male mammals which comprises administering systemically to male mammals a sterilizing amount of a compound of the Formula I.

5 Claims, No Drawings

METHOD OF PRODUCING INFERTILITY IN MALE RODENTS

This is a continuation of application Ser. No. 736,943, filed Oct. 29, 1976, now abandoned, which is a division of application Ser. No. 601,487, filed Aug. 4, 1975, now U.S. Pat. No. 4,012,520, which is a division of application Ser. No. 386,536, filed Aug. 8, 1973, now U.S. Pat. No. 3,930,012, which is a continuation of application Ser. No. 93,383, filed Nov. 27, 1970, now abandoned.

BRIEF SUMMARY OF THE INVENTION

This invention relates to pharmaceutical preparations and methods of use thereof. The pharmaceutical preparations are compounded with edible and injectable carriers to prepare baits, capsules, both hard and soft, suspensions, and injectables. The preparations contain an effective amount of a compound of the Formula 1 for bringing about sterility in the male mammals, for example, monkeys, rats, hamsters and guinea pigs.

DETAILED DESCRIPTION

The compounds of the Formula 1 can be prepared by methods known in the art. For example, a compound of Formula 1 wherein X is

can be prepared by reacting epichlorohydrin with carbon dioxide in the presence of a catalyst in accordance with U.S. Pat. Nos. 2,873,282 and 2,773,070, or by reacting 3-chloro-1,2-propanediol with phosgene, Contardi and Ercoli, Gazz. Chim. Ital. 64, 522 (1934), C. A. 29, 1392.

Compounds wherein X is

G. A. Rezuvaev, V. S. Etlis, and L. N. Grobov, J. Gen. Chem. (USSR 32, 1979 (1962). Another method is by the reaction of 3-chloro-1,2,-propanediol with thiophosgene.

Acetals and ketals wherein X is

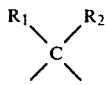

and $R_1$ and $R_2$ are as previously defined are prepared by reacting 3-chloro-1,2-propanediol with a carbonyl compound of the Formula

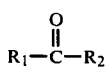

in the presence of an acid catalyst. Synthetic Organic Chemistry, Wagner and Zook, 252 (1953) J. Wiley & Sons, Inc.

The pharmaceutical preparations are compounded along with suitable oral and injectable carriers to prepare the aforesaid dosage forms. The capsules for oral use are hard gelatin capsules or soft gelatin capsules, containing the active ingredient alone or admixed with an edible oily medium, for example, cottonseed oil, peanut oil, and mineral oil. Elixirs and syrups are formulated with suitable sweetening agents, for example, saccharin and sucrose, and diluents such as ethanol, glycerol and sorbitol. They may contain a demulcent and are preferably flavored and colored to provide orally acceptable preparations. Advantageously they contain a suitable preservative such as methyl- or propylparaben. Emulsions suitable for oral use are of both the oil/water and water/oil types. Also, the essential active ingredient may be in the form of a water-insoluble liquid which is dispersed in the emulsion bases. The emulsions contain emulsifying agents such as acacia and tragacanth and surfactants, for example, polysorbate 80 and poloxalkol. Solutions of the water-soluble compounds are prepared by simple admixture with water which advantageously contains a preservative such as methyl- or propylparaben. Oil dispersions contain the essential active ingredient and may include a demulcent, for example, methyl-cellulose, alginate, polyvinylpyrrolidone, along with a dispersing agent such as lecithin. The dispersions also contain suitable preservatives, for example, propylparaben. Dosage forms for injectable use are sterile solutions, the pure compound in sterile form, and sterile emulsions. Such preparations for injectable use must be sterile and must contain bacteriostatic preservative agents according to the art.

Oral dosage forms, as heretofore described, contain from about 0.008 to about 1.0 gm. of the essential active ingredient per unit dose, but are not limited thereto, since within such range they include, for example, 0.01 gm., 0.08 gm., and 0.5 gm. Sterile liquid forms for injectable administration containing from about 10 to 85% of the essential active ingredient but are not limited thereto, since they include within this range, for example, 25%, 50%, and 75%. Liquid oral dosage forms contain from About 5% to 85% of the essential active ingredient but are not limited thereto, since within this range are included, for example 10%, 25%, 50%, and 75%. These dosage forms provide, generally, a dosage range of essential active ingredient from about 0.008 to about 1.0 gm. per day. The daily oral and parenteral doses are approximately the same except for sustained parenteral dosage forms which contain from about 0.25 gm. to about 4.0 gm. of essential active ingredient per ml. and are given once a month intramuscularly. The usual oral and parenteral forms are to be administered once per day. Other ingredients, which are, however, not essential to the present invention, are, for example, a progestational agent such as medroxyprogesterone or melengestro acetate, given in the usual dosage regime for such active ingredient.

Mature virgin male rats are checked for ability to mate by placement with immature female rats primed with gonadotropic factor of pregnant mare's serum. Those males which mate are used for subcutaneous injection or oral administration of the novel pharmaceutical preparations. The essential active ingredient is prepared as a 5.0 mg./ml. dipersion in 0.25% aqueous methylcellulose in sterile vehicle. This pharmaceutical composition is administered to each of three mature mating males, a half ml. per day subcutaneously or orally for eight days. These treated males are exposed to receptive mature females for mating and mating is checked by the presence of sperm with or without a plug in the vagina of the female. Approximately ten days thereafter, the females are examined for the presence and number of implantation sites, and the ability of the pharmaceutical compositions to prevent impregnation by the mature male is shown by the absence of implantation sites at autopsy.

The following examples illustrate the manner and process of making and using the invention but are not to be construed as limiting.

EXAMPLE 1

4-(Chloromethyl)-2-(oxo)-1 3-dioxolane was prepared as a 1.0% sterile dispersion in 0.25% aqueous methylcellulose. One-half ml. was injected subcutaneously into each of three mating male rats for eight days. Thereafter, the treated males were subjected to the aforesaid procedure to determine the ability of the preparation to prevent impregnation by the males, and the preparation was found to be effective.

EXAMPLE 2

4-(Chloromethyl)-2,2,dimethyl-1,3-dioxolane oil dispersion in the form of a pharmaceutical preparation, provided an oral pharmaceutical preparation effective in preventing implantation.

EXAMPLE 3

The 4-(chloromethyl)-2,2,diphenyl- and 4-(chloromethyl)-2-(2-furyl)-1,3-dioxolanes were likewise tested according to procedures given heretofore and found capable of preventing impregnation by the male.

EXAMPLE 4

An oral pharmaceutical preparation containing 1.0% of 4-(chloromethyl)-2,2-dimethyl-1,3-dioxolane in 0.25% aqueous methylcellulose was administered orally to mating mature male rats daily for seven weeks at a daily dose of 5 mg. per rat. This preparation induced inability in the male to impregnate receptive females by the first week and this infertility remained throughout the treatment.

EXAMPLE 5

A sterile aqueous dispersion for injectable use is prepared to contain 100 mg./ml. of 4-(chloromethyl)-2-oxo-1,3-dioxolane. The injection of 2.5 ml. per day is effective to prevent impregnation of receptive female monkeys by a mature male.

Additional embodiments of the present inventive concept are baits, i.e., rations, for oral ingestion by rodents, especially rats, and methods of controlling rodent population, especially the rat population. Such rations contain the essential active ingredient and, in amounts that are attractive to the animals in the sense that they are not repelled thereby, edible dietary constitutents such as protein, fat, carbohydrate, minerals and vitamins.

This medicated ration must not repel the rodents although it does not necessarily have to attractin the sense of being absolutely preferred over other rations. Hence, the medicated ration retains the natural flavor of dietary constitutents after the essential active ingredient is incorporated therein. Such incorporation provides a final mixture or blend throughout which the active ingredient is uniformly distributed. Such active ingredient can be added to the ration by mixing both as solids or as liquids, by addition to a solid ration of a solution or suspension in water or ethanol; by adding the active ingredient in a liquid which is then removed to leave a dry solid mixture, for example, a solution or suspension in water or ethanol; by adding the active ingredient in the form of coated particles or pellets, coated, for example, by coacervation with gelatin, or by coating with an alcohol solution of a water-soluble type of ethyl cellulose. The final ration containing the coated particles or pellets is in the preferred form because of its tendency to better mask any undesirable taste of the essential active ingredient. The rations contain the essential active ingredient in a concentration sufficient to cause lesions in the excurrent duct (epididymal lesions) and permanent infertility in otherwise fertile male animals, especially rats, when they ingest the compositions in their usual manner of providing for their metabolic needs. Illustratively, most mature male rats that ingest an amount of the ration providing at least about 5.0 mg. per kilogram of rat body weight become irreversibly infertile as shown by epididymal lesions and by sterile mating with fertile females. As will be apparent, rats eating ad libitum will consume different amounts of the active ingredient-containing rations. Hence, to provide about 100 mg per kilogram in a rat eating a smaller amount of the effective ration, a more concentrated ration must be provided than for a rat consuming a larger amount of the same ration. In the latter case, a less concentrated ration is operable. For example, in rats weighing about 200 to 250 gm. and consuming about 10 to 25 gm. of ration at one feeding, the ration may contain 1.0% by weight of the active ingredient. Thereby, the 250 gm. rat consuming 10 gm. of the treated edible preparation ingests 100 mg of the active ingredient equivalent to about 400 mg per kilo. With this same ration containing 1.0% active ingredient, a 200 gm. rat eating 25 gm. at one feeding ingests 250 mg. of the active ingredient, equivalent to about 1000 mg. per kilo. Such variations will occur due to the eating habits of the rats. Hence, various embodiments of the rodent-control preparations are within the inventive concept provided they contain an effective amount of the essential active ingredient to cause the males to acquire the epididymal lesions of infertility.

The aforesaid embodiments of this invention concept provide a method of controlling fertility of male rodents, especially rats, which consists essentialy of providing in locales available to and frequented by said male rodents rations supplying an effective amount of a compound of the Formula I. Preferably, the rations supply to the recipient at least about 5.0 mg./kg. of body weight thereof. At this level most rats acquire irreversible infertility and a reduction in rat population ensues in times. Expressed as percentage by weight of the edible composition, the active ingredient amounts to from about 0.05% to about 0.5%, such range being not limited thereto for it includes within the range the other percentages such as 0.01%, 0.02%, 0.03%, and 0.04%. A more concentrated preparation, say up to about 1% or even 5%, is satisfactory provided it is, upon use, diluted with the aforesaid edible dietary constituents to provide operative amounts of the essential active ingredient without wasting active material. These embodiments of the inventive concept are made available to the animals, especially rats, for control of the population thereof by placing the preparation in and about the locales available to and frequented by the rodents.

I claim:

1. A method of producing epididymal lesions and infertility in male rodents which comprises supplying to said rodents in locales available to and frequented by said rodents a ration supplying an effective amount for producing the lesions and infertility of a compound of the formula:

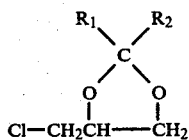

wherein $R_1$ and $R_2$ are the same or different and are hydrogen, alkyl of from 1 to 17 carbon atoms, alkenyl of from 2 to 17 carbon atoms, phenyl, furyl or thienyl, and $R_1$ and $R_2$, taken together, can be a carbocyclic ring of up to 8 carbon atoms.

2. The method of claim 1 wherein the compound is 4-(chloromethyl)-2,2-dimethyl-1,3-dioxolane.

3. The method of claim 1 wherein the compound is 4-(chloromethyl)-2,2-diphenyl-1,3-dioxolane.

4. The method of claim 1 wherein the compound is 4-(chloromethyl)-2-(2-furyl)-1,3-dioxolane.

5. The method of claim 1 wherein the effective amount is at least about 5.0 mg./kg of body weight of said male rodents.

* * * * *

UNITED STATES PATENT OFFICE
CERTIFICATE OF CORRECTION

Patent No. 4,196,213   Dated April 1, 1980

Inventor(s) Gilbert A. Youngdale

It is certified that error appears in the above-identified patent and that said Letters Patent are hereby corrected as shown below:

Column 1, line 45: "Rezuvaev" should read -- Razuvaev --.
Column 1, line 46: "(USSR 32," should read -- (USSR) 32, --.
Column 1, line 65: "252" should read -- 262 --.
Column 2, line 55: "melengestro" should read -- melengestrol --.
Column 2, line 63: "dipersion" should read -- dispersion --.
Column 3, line 60: "attractin the" should read -- attract in the --.
Column 4, line 54: "times." should read -- time. --.
Column 4, line 56: "0.05%" should read -- .05% --.
Column 4, line 58: "0.01%, 0.02%, 0.03%, and 0.04%." should read -- .01%, .02%, .03%, and .04%. --.

Signed and Sealed this

Twenty-eighth Day of July 1981

[SEAL]

Attest:

Attesting Officer

GERALD J. MOSSINGHOFF

Commissioner of Patents and Trademarks